US006725082B2

(12) United States Patent
Sati et al.

(10) Patent No.: US 6,725,082 B2
(45) Date of Patent: Apr. 20, 2004

(54) SYSTEM AND METHOD FOR LIGAMENT GRAFT PLACEMENT

(75) Inventors: Marwan Sati, Olten (CH); Peter Lutz Nolte, Hunibach (CH)

(73) Assignee: Synthes U.S.A., Paoli, PA (US)

( * ) Notice: Subject to any disclaimer, the term of this patent is extended or adjusted under 35 U.S.C. 154(b) by 0 days.

(21) Appl. No.: 09/953,366

(22) Filed: Sep. 17, 2001

(65) Prior Publication Data

US 2002/0055679 A1 May 9, 2002

Related U.S. Application Data

(63) Continuation of application No. PCT/EP99/01778, filed on Mar. 17, 1999.

(51) Int. Cl.⁷ ............................................. A61B 5/05
(52) U.S. Cl. ................ 600/429; 600/407; 600/424; 600/426; 600/438; 606/130
(58) Field of Search .................. 378/42, 163, 205, 378/207, 51, 63, 62; 600/407, 424, 425, 426, 427, 429, 437, 438; 606/130, 96, 88; 430/966; 128/920; 602/424

(56) References Cited

U.S. PATENT DOCUMENTS

| 3,821,469 A | 6/1974 | Whetstone et al. .......... 178/18 |
| 3,983,474 A | 9/1976 | Kuipers ..................... 324/43 |
| 4,058,114 A | 11/1977 | Soldner ....................... 128/2 |
| 4,146,924 A | 3/1979 | Birk et al. ................. 364/513 |
| 4,182,312 A | 1/1980 | Mushabac .................... 433/68 |
| 4,204,225 A | 5/1980 | Mistretta ................... 358/111 |
| 4,209,254 A | 6/1980 | Reymond et al. ........... 356/152 |
| 4,262,306 A | 4/1981 | Renner ....................... 358/93 |
| 4,341,220 A | 7/1982 | Perry ........................ 128/630 |
| 4,358,856 A | 11/1982 | Stivender et al. .......... 378/167 |
| 4,396,945 A | 8/1983 | DiMatteo et al. ........... 358/107 |
| 4,418,422 A | 11/1983 | Richter et al. ............. 378/205 |
| 4,419,012 A | 12/1983 | Stephenson et al. ........ 356/141 |
| 4,437,161 A | 3/1984 | Anderson ................... 364/414 |
| 4,457,311 A | 7/1984 | Sorenson et al. ........... 128/660 |
| 4,465,069 A | 8/1984 | Barbier et al. ............. 128/303 |
| 4,473,074 A | 9/1984 | Vassiliadis ............... 128/303.1 |

(List continued on next page.)

FOREIGN PATENT DOCUMENTS

| DE | 195 06 197 A1 | 5/1996 |
| DE | 195 36 180 A1 | 6/1997 |

(List continued on next page.)

OTHER PUBLICATIONS

Nolte et al., "Clinical Evaluation of a System for Precision Enhancement in Spine Surgery," *Clinical Biomechanics*, vol. 10, No. 6, pp. 293–303 (1995).

(List continued on next page.)

*Primary Examiner*—David V. Bruce
*Assistant Examiner*—Allen C. Ho
(74) *Attorney, Agent, or Firm*—Jones Day

(57) ABSTRACT

The present invention relates to a method for obtaining data indicative of a location for ligament graft placement. Medical image data representative of a bone is provided. Position data indicative of an intraoperative position of each of a plurality of points associated with a surface of the bone is obtained. The medical image data and the position data are related to one another mathematically to obtain transformed data indicative of the location for ligament graft placement. The present invention is also related to a system for obtaining data indicative of a location for ligament graft placement. The system includes a computer configured to receive medical image data representative of a bone and a pointer or ultrasound device configured to determine position data indicative of an intraoperative position of one or more points associated with a surface of the bone.

27 Claims, 1 Drawing Sheet

U.S. PATENT DOCUMENTS

| | | | |
|---|---|---|---|
| 4,485,815 A | 12/1984 | Amplatz et al. | 128/329 |
| 4,543,959 A | 10/1985 | Seponen | 128/653 |
| 4,571,834 A | 2/1986 | Fraser et al. | 33/1 |
| 4,583,538 A | 4/1986 | Onik et al. | 128/303 |
| 4,592,352 A | 6/1986 | Patil | 128/303 |
| 4,598,368 A | 7/1986 | Umemura | 364/414 |
| 4,602,622 A | 7/1986 | Bär et al. | 128/303 |
| 4,613,866 A | 9/1986 | Blood | 343/448 |
| 4,613,942 A | 9/1986 | Chen | 364/513 |
| 4,618,978 A | 10/1986 | Cosman | 378/164 |
| 4,638,798 A | 1/1987 | Shelden et al. | 128/303 |
| 4,649,504 A | 3/1987 | Krouglicof et al. | 364/559 |
| 4,651,732 A | 3/1987 | Frederick | 128/303 |
| 4,670,781 A | 6/1987 | Aubert et al. | 358/93 |
| 4,672,564 A | 6/1987 | Egli et al. | 364/559 |
| 4,674,057 A | 6/1987 | Caughman et al. | 364/513 |
| 4,729,098 A | 3/1988 | Cline et al. | 364/414 |
| 4,733,661 A | 3/1988 | Palestrant | 128/303 |
| 4,733,969 A | 3/1988 | Case et al. | 356/375 |
| 4,737,032 A | 4/1988 | Addleman et al. | 356/376 |
| 4,742,815 A | 5/1988 | Ninan et al. | 128/4 |
| 4,743,770 A | 5/1988 | Lee | 250/560 |
| 4,743,771 A | 5/1988 | Sacks et al. | 250/560 |
| 4,745,290 A | 5/1988 | Frankel et al. | 250/360 |
| 4,750,487 A | 6/1988 | Zanetti | 128/303 |
| 4,753,528 A | 6/1988 | Hines et al. | 356/1 |
| 4,760,851 A | 8/1988 | Fraser et al. | 128/774 |
| 4,761,072 A | 8/1988 | Pryor | 356/1 |
| 4,762,016 A | 8/1988 | Stoughton et al. | 74/479 |
| 4,763,652 A | 8/1988 | Brisson et al. | 128/328 |
| 4,764,016 A | 8/1988 | Johansson | 356/371 |
| 4,776,749 A | 10/1988 | Wanzenberg et al. | 414/680 |
| 4,779,212 A | 10/1988 | Levy | 364/562 |
| 4,782,239 A | 11/1988 | Hirose et al. | 250/561 |
| 4,791,934 A | 12/1988 | Brunnett | 128/653 |
| 4,793,355 A | 12/1988 | Crum et al. | 128/653 |
| 4,794,262 A | 12/1988 | Sato et al. | 250/560 |
| 4,803,976 A | 2/1989 | Frigg et al. | 128/92 |
| 4,821,200 A | 4/1989 | Öberg | 364/474.24 |
| 4,821,206 A | 4/1989 | Arora | 364/513 |
| 4,822,163 A | 4/1989 | Schmidt | 356/1 |
| 4,825,091 A | 4/1989 | Breyer et al. | 250/560 |
| 4,829,373 A | 5/1989 | Leberl et al. | 358/88 |
| 4,835,710 A | 5/1989 | Schnelle et al. | 364/513 |
| 4,836,778 A | 6/1989 | Baumrind et al. | 433/69 |
| 4,841,967 A | 6/1989 | Chang et al. | 128/303 |
| 4,869,247 A | 9/1989 | Howard, III et al. | 128/303.1 |
| 4,875,478 A | 10/1989 | Chen | 128/303 |
| 4,896,673 A | 1/1990 | Rose et al. | 128/660.03 |
| 4,907,252 A | 3/1990 | Aichinger et al. | 378/99 |
| 4,943,296 A | 7/1990 | Funakubo et al. | 606/166 |
| 4,945,914 A | 8/1990 | Allen | 128/653 |
| 4,955,891 A | 9/1990 | Carol | 606/130 |
| 4,970,666 A | 11/1990 | Welsh et al. | 364/522 |
| 4,987,488 A | 1/1991 | Berci | 358/93 |
| 4,991,579 A | 2/1991 | Allen | 128/653 |
| 5,016,639 A | 5/1991 | Allen | 128/653 |
| 5,027,818 A | 7/1991 | Bova et al. | 128/653 |
| 5,037,426 A * | 8/1991 | Goble et al. | 606/96 |
| 5,047,036 A | 9/1991 | Koutrouvelis | 606/130 |
| 5,050,608 A | 9/1991 | Watanabe et al. | 128/653 |
| 5,059,789 A | 10/1991 | Salcudean | 250/206.1 |
| 5,078,140 A | 1/1992 | Kwoh | 128/653.1 |
| 5,080,662 A | 1/1992 | Paul | 606/130 |
| 5,086,401 A | 2/1992 | Glassman et al. | 395/94 |
| 5,094,241 A | 3/1992 | Allen | 128/653.1 |
| 5,097,839 A | 3/1992 | Allen | 128/653.1 |
| 5,099,846 A | 3/1992 | Hardy | 128/653 |
| 5,107,839 A | 4/1992 | Houdek et al. | 128/653.1 |
| 5,119,817 A | 6/1992 | Allen | 128/653.1 |
| 5,142,930 A | 9/1992 | Allen et al. | 74/469 |
| 5,178,164 A | 1/1993 | Allen | 128/898 |
| 5,186,174 A | 2/1993 | Schlöndorff et al. | 128/653.1 |
| 5,197,476 A | 3/1993 | Nowacki et al. | 128/660.03 |
| 5,198,877 A | 3/1993 | Schulz | 356/375 |
| 5,207,223 A | 5/1993 | Adler | 128/653.1 |
| 5,211,164 A | 5/1993 | Allen | 128/653.1 |
| 5,211,165 A | 5/1993 | Dumoulin et al. | 128/653.1 |
| 5,230,338 A | 7/1993 | Allen et al. | 128/653 |
| 5,230,623 A | 7/1993 | Guthrie et al. | 433/72 |
| 5,249,581 A | 10/1993 | Horbal et al. | 128/664 |
| 5,251,127 A | 10/1993 | Raab | 364/413.13 |
| 5,257,998 A | 11/1993 | Ota et al. | 606/130 |
| 5,274,551 A | 12/1993 | Corby, Jr. | 364/413.13 |
| 5,278,756 A | 1/1994 | Lemchen et al. | 364/413.28 |
| 5,295,483 A | 3/1994 | Nowacki et al. | 128/660.03 |
| 5,299,288 A | 3/1994 | Glassman et al. | 395/80 |
| 5,300,080 A | 4/1994 | Clayman et al. | 606/130 |
| 5,305,203 A | 4/1994 | Raab | 364/413.13 |
| 5,309,913 A | 5/1994 | Kormos et al. | 128/653.1 |
| 5,325,855 A | 7/1994 | Daghighian et al. | 128/653.1 |
| 5,350,351 A | 9/1994 | Saffer | 601/2 |
| 5,383,454 A | 1/1995 | Bucholz | 128/653.1 |
| 5,389,101 A | 2/1995 | Heilbrun et al. | 606/130 |
| 5,394,457 A | 2/1995 | Leibinger et al. | 378/162 |
| 5,408,409 A | 4/1995 | Glassman et al. | 364/413.13 |
| 5,445,166 A | 8/1995 | Taylor | 128/897 |
| 5,479,597 A | 12/1995 | Fellous | 395/154 |
| 5,483,961 A | 1/1996 | Kelly et al. | 128/653.1 |
| 5,494,034 A | 2/1996 | Schlöndorff et al. | 128/653.1 |
| 5,517,990 A | 5/1996 | Kalfas et al. | 128/653.1 |
| 5,531,751 A * | 7/1996 | Schultheiss et al. | 606/104 |
| 5,588,430 A | 12/1996 | Bova et al. | 128/653.1 |
| 5,617,857 A | 4/1997 | Chader et al. | 128/653.1 |
| 5,622,170 A | 4/1997 | Schulz | 128/653.1 |
| 5,630,431 A | 5/1997 | Taylor | 128/897 |
| 5,631,973 A | 5/1997 | Green | 382/128 |
| 5,662,111 A | 9/1997 | Cosman | 128/653.1 |
| 5,676,673 A | 10/1997 | Ferre et al. | 606/130 |
| 5,682,886 A * | 11/1997 | Delp et al. | 128/920 |
| 5,711,299 A | 1/1998 | Manwaring et al. | 128/653.1 |
| 5,729,129 A | 3/1998 | Acker | 324/207.12 |
| 5,732,703 A | 3/1998 | Kalfas et al. | 128/653.2 |
| 5,735,278 A | 4/1998 | Hoult et al. | 128/653.2 |
| 5,748,767 A | 5/1998 | Raab | 382/128 |
| 5,755,725 A | 5/1998 | Druais | 606/130 |
| RE35,816 E | 6/1998 | Schulz | 356/376 |
| 5,769,078 A | 6/1998 | Kliegis | 128/653.1 |
| 5,769,789 A | 6/1998 | Wang et al. | 600/414 |
| 5,769,861 A | 6/1998 | Vilsmeier | 606/130 |
| 5,772,593 A | 6/1998 | Hakamata | 600/407 |
| 5,795,294 A | 8/1998 | Luber et al. | 600/407 |
| 5,799,099 A | 8/1998 | Wang et al. | 382/131 |
| 5,800,352 A | 9/1998 | Ferre et al. | 600/407 |
| 5,807,252 A | 9/1998 | Hassfeld et al. | 600/407 |
| 5,810,008 A | 9/1998 | Dekel et al. | 128/660.07 |
| 5,817,022 A | 10/1998 | Vesely | 600/443 |
| 5,829,444 A | 11/1998 | Ferre et al. | 128/897 |
| 5,848,967 A | 12/1998 | Cosman | 600/426 |
| 5,880,976 A | 3/1999 | DiGioia III et al. | 364/578 |
| 5,995,738 A | 11/1999 | DiGioia, III et al. | 395/500.32 |
| 6,002,859 A | 12/1999 | DiGioia, III et al. | 395/500.32 |
| 6,021,343 A | 2/2000 | Foley et al. | 600/429 |
| 6,112,113 A | 8/2000 | Van Der Brug et al. | 600/427 |
| 6,120,465 A | 9/2000 | Gunthrie et al. | 600/587 |
| 6,122,341 A | 9/2000 | Butler et al. | 378/20 |
| 6,135,946 A | 10/2000 | Konen et al. | 600/117 |
| 6,149,592 A | 11/2000 | Yanof et al. | 600/427 |
| 6,165,181 A | 12/2000 | Heilbrun et al. | 606/130 |
| 6,167,145 A | 12/2000 | Foley et al. | 382/128 |

| | | | |
|---|---|---|---|
| 6,167,295 A | 12/2000 | Cosman | 600/426 |
| 6,167,296 A | 12/2000 | Shahidi | 600/427 |
| 6,190,320 B1 | 2/2001 | Lelong | 600/439 |
| 6,190,395 B1 | 2/2001 | Williams | 606/130 |
| 6,198,794 B1 | 3/2001 | Peshkin et al. | 378/42 |
| 6,205,411 B1 | 3/2001 | DiGioia, III et al. | 703/11 |
| 6,216,029 B1 | 4/2001 | Paltieli | 600/427 |
| 6,224,613 B1 | 5/2001 | Hofstetter | 606/130 |
| 6,226,548 B1 | 5/2001 | Foley et al. | 600/426 |
| 6,233,476 B1 | 5/2001 | Strommer et al. | 600/424 |
| 6,236,875 B1 | 5/2001 | Bucholz et al. | 600/407 |
| 6,241,735 B1 | 6/2001 | Marmulla | 606/102 |
| 6,246,898 B1 | 6/2001 | Vesely et al. | 600/424 |
| 6,256,529 B1 | 7/2001 | Holupka et al. | 600/427 |
| 6,259,943 B1 | 7/2001 | Cosman et al. | 600/429 |
| 6,275,725 B1 | 8/2001 | Cosman | 600/426 |
| 6,285,902 B1 | 9/2001 | Kienzle, III et al. | 600/427 |
| 6,298,262 B1 | 10/2001 | Franck et al. | 600/426 |
| 6,317,616 B1 | 11/2001 | Glossop | 600/407 |
| 6,332,891 B1 | 12/2001 | Himes | 606/169 |
| 6,341,231 B1 | 1/2002 | Ferre et al. | 600/424 |
| 6,351,659 B1 | 2/2002 | Vilsmeier | 600/407 |
| 6,351,662 B1 | 2/2002 | Franck et al. | 600/429 |
| 6,533,737 B1 * | 3/2003 | Brosseau et al. | 600/595 |
| 2001/0007919 A1 | 7/2001 | Shahidi | 600/427 |
| 2001/0021806 A1 | 9/2001 | Gueziec et al. | 600/425 |
| 2001/0027271 A1 | 10/2001 | Franck et al. | 600/426 |
| 2001/0039421 A1 | 11/2001 | Heilbrun et al. | 606/130 |

FOREIGN PATENT DOCUMENTS

| | | |
|---|---|---|
| DE | 297 04 393 U1 | 7/1997 |
| EP | 0 062 941 A1 | 10/1982 |
| EP | 0 326 768 A2 | 8/1989 |
| EP | 0 591 712 A1 | 4/1994 |
| EP | 0603 089 | 6/1994 |
| EP | 0 647 428 A2 | 4/1995 |
| EP | 0 832 609 A2 | 4/1998 |
| GB | 2 094 590 A | 9/1982 |
| WO | WO 90/05494 | 5/1990 |
| WO | WO 91/07726 | 5/1991 |
| WO | WO 94/23647 | 10/1994 |
| WO | WO 94/24933 | 11/1994 |
| WO | WO 95/15729 | 6/1995 |
| WO | WO 95/31148 | 11/1995 |
| WO | WO 96/11624 | 4/1996 |
| WO | WO 97/29685 | 8/1997 |
| WO | WO 97/29709 | 8/1997 |
| WO | WO 97/47240 | 12/1997 |

OTHER PUBLICATIONS

Lavallée et al., "Computer Assisted Kneww Anterior Cruciate Ligament Reconstruction First Clinical Tests," *TIMC–IMAG, Faculté de Médecine de Grenoble*, pp. 11–16.

* cited by examiner

SYSTEM AND METHOD FOR LIGAMENT GRAFT PLACEMENT

RELATED APPLICATIONS

This application is a continuation of prior application No. PCT/EP99/01778 filed Mar. 17, 1999, which is incorporated herein by reference in its entirety.

FIELD OF THE INVENTION

The present invention relates to a method and system for computerized in-situ planning and guidance of ligament graft placement.

BACKGROUND OF THE INVENTION

Treatment of injuries and other conditions associated with a joint of an individual often involves the re-attachment or reconstruction of one or more ligaments. For example, anterior cruciate ligament (ACL) rupture is a very common sports-related injury. Ligament reconstruction with autogenous graft using a minimally invasive endoscopic approach has become a standard therapy in ACL replacement. Endoscopic surgical approaches seek to minimize trauma to the individual.

Unfortunately, approximately 40% of ACL ligaments are improperly located, e.g., misplaced as a result of reconstructions performed by traditional endoscopy. Such improper ligament placement can lead to premature degeneration of knee structures, which degeneration can eventually necessitate total knee joint replacement. To facilitate proper ligament placement, a practitioner is preferably able to identify and locate anatomical landmarks associated with the joint. For example, proper ligament reconstruction or positioning involves steps such as the drilling of tunnels that are properly placed with respect to the anatomical landmarks, avoiding the impingement of ligaments and surrounding tissues, ensuring that ligament elongation does not exceed 10% (collagen fibre ruptures beyond 10% elongation), selecting proper graft tension and position to restore knee stability; and obtaining proper graft fixation in good quality bone.

A portion of ligament misplacements are attributable to the restricted, local endoscopic view, which fails to provide surgeons with a global overview of ligament position, such as that seen in traditional postoperative X-rays. For example, the endoscopic view limits a surgeon's ability to identify landmarks, which would otherwise assist in proper ligament placement.

A method for determining the femoral point of graft attachment during ACL replacement is disclosed in European Patent Application No. 0603089 to Cinquin et al. The disclosed method concerns the determination of a femoral point of graft attachment with respect to a tibial graft attachment point such that the distance between these two points remains invariant during knee flexion and extension. The positions within an on-site three-dimensional coordinate system of a reference and a pointer, which are both provided with energy emitting markers, are determined by means of a three-dimensional position measurement system, such as the OPTOTRAK position measurement system, Northern Digital, Waterloo, On. The position measurement system measures the position of the markers with respect to the on-site three-dimensional coordinate system. Therewith, the position of the tip of the pointer is determinable by means of a computer.

The Cinquin method comprises the steps of (1) attachment of a first reference at the tibia; (2) positioning of the pointer tip at a previously determined point $T_1$ and measuring the position of the pointer tip with respect to the first reference; (3) Positioning of the pointer tip at several points $P_1$ at the trochlea of the femur close to that position where the invariant point is expected; (4) Calculation of the distances of point $T_1$ and each of the points P1; (5) Displacement of the femur with respect to the tibia and calculation of the variations of the distances between $T_1$ and each of the points $P_1$; (6) Selection of that point $P_1$ among points $P_1$ which shows the most invariant distance.

The Cinquin method measures knee movement to obtain a "functional" placement of the ligament that respects certain elongation criteria. The disadvantage of this method is that anatomical placement criteria such as a general overview of graft position with respect to the whole anatomy of the joint are not obtained.

BRIEF SUMMARY OF THE INVENTION

The present invention is related to a ligament replacement system, which allows both consideration of functional and anatomical criteria in a variety of graft types, surgical philosophies and surgical techniques. The system preferably provides realtime computerized in-situ planning and guidance of ligament graft placement. Most preferably, the system provides planning and guidance for anterior cruciate ligament insertion.

One embodiment of the system comprises a position measurement device in communication with a computer to determine the position and orientation of objects in a three dimensional coordinate system. The three dimensional coordinate system includes at least one organ, such as a femur or tibia, of an individual. Objects to be tracked comprise at least three markers, which can be configured to emit, receive, or reflect energy, such as light or acoustic energy. For example, energy emitters can include light sources, such as light emitting diodes emitting in the visible or infrared, acoustic transmitters, or conductive coils suitable for establishing a detectable magnetic field. Energy receiving means include light detectors, such as photodiodes or charge coupled devices. Microphones or Hall-effect elements may also be used.

To sense the position of energy emitting markers, the system includes at least three energy detecting elements, such as three light detectors. The three energy detecting elements cooperate with the energy emitting markers to determine the position of each marker associated with an object to be tracked. Based on the respective positions of markers associated with the tracked object, the position and orientation of the tracked object are determined.

The system preferably includes a plurality of reference bodies, which can be used to determine the position and orientation of an organ of an individual. The reference bodies are preferably rigid, having at least three markers each. Each reference body preferably comprises an attachment element, such as a screw or pin, with which the reference bodies can be attached to an organ, such as a bone. For example, respective reference bodies can be attached to the femur and tibia. In one embodiment, the reference markers are fiducial markers.

The system also includes a pointer and an endoscope. The pointer includes markers, which allow the position and orientation of the pointer to be determined. The pointer includes a pointer tip having a known spatial relationship to the markers. Thus, the position of the pointer tip can be determined from the positions of the markers. The endoscope preferably includes markers that allow the position and orientation of the endoscope to be determined in the three dimensional coordinate system. In a preferred embodiment, the pointer and endoscope are integral with one another.

The computer is configured to determine the position and orientation of the reference bodies, endoscope, and pointer based upon the position and orientation of the associated markers. The pointer and the endoscope are preferably configured as a one-piece computer-integrated endoscopic instrument.

An embodiment of the system includes a medical imaging device, which preferably includes an X-ray source and an X-ray receiver, for gathering medical image data, which is transferred to the computer either directly in numerical format or upon digitizing a radiographic film of the image. The computer is configured to process the image such as by magnifying a portion of the image. The imaging device can be used preoperatively and/or intraoperatively.

In a preferred embodiment, the system includes an ultrasound device, having associated markers, which allow the position and orientation of an ultrasound head of the ultrasound device to be determined as discussed above. The ultrasound device is in communication with the computer, which can process and display ultrasound data acquired by the ultrasound device. In a preferred embodiment the ultrasound device is an A-mode ultrasound device configured to emit and receive an ultrasound beam along a preferably known axis to allow realtime signal processing and or display of ultrasound data.

The computer is preferably configured, such as with a memory or software, to display a three-dimensional representation of the connection between ligament attachment points determined using the pointer. When ligament attachment points are identified, the computer can display a preferably three dimensional representation of the connection between ligament attachment points previously determined using the pointer or ultrasound device. The computer is preferably configured to display a ligament during knee flexion and extension.

One embodiment of the system further comprises a drilling device having at least three markers. The drilling device has a drill tip having a known spatial relationship relative to the markers. The drilling device markers allow the position and orientation of the drilling device and drill tip to be determined in the three dimensional coordinate system. Thus, the position of the drill tip can be determined relative to a predetermined location of a patient's bone. For example, the drill tip can be positioned relative to the bone as previously planned using the computer. The computer is preferably configured to allow at least one of the image data and ultrasound data to be used to plan the position and orientation (path) of a hole to be drilled. The path of a hole being bored by the drill can be monitored and displayed by the computer. Thus, the actual path can be compared to the previously planned drill path to allow the practitioner to minimize deviations between the actual procedure and the preoperative plan. In one embodiment the drill is guided to allow the computer to control the drilling path.

Another embodiment of the invention relates to a method for ligament reconstruction. The method comprises obtaining medical image data, such as at least one X-ray of a joint associated with the ligaments. For example, if the ligaments of the knee are to be reconstructed, the medical image data comprises respective portions of both the femur and tibia. The medical image data is transferred to a computer. Based upon the medical image data, ligament graft placement with respect to anatomical landmarks of the first and second bones is determined based upon computer manipulation of the medical image data. Preferably the medical image data are prepared as one or more templates.

The positions of the landmarks, such as points, on the surface of first and second bones of an individual are determined with respect to a three dimensional coordinate system. In a preferred embodiment, the first and second bones are respectively the femur and tibia of an individual. The determination of the landmark positions preferably comprises use of at least one of an ultrasound device and a pointer.

The ultrasound device, which is in communication with the computer, is used to provide ultrasound data of the first and second bones. The ultrasound device includes markers that allow a position measuring device to determine the position and orientation of the ultrasound device to be determined in the three dimensional coordinate system. The ultrasound data preferably comprises data indicative of the position of landmarks of the first and second bones. For example, the ultrasound data preferably comprises data indicative of a position of at least one of the posterior femoral and tibial condyles.

The pointer comprises a pointer tip, which can be positioned relative to a landmark. The position measurement system is used to determine the position and orientation of markers associated with the pointer. Based on the known position and orientation of the markers of the pointer, the position and orientation of the pointer tip can be determined. The position of the landmark on the surface of the first and second bones are determined based on the spatial relationship between the pointer tip and the landmark.

Based upon the landmark position data, a mathematical relationship between the intraoperative position of the first and second bones and an image of the first and second bones from at least one of the medical image data and ultrasound data is determined. Preferably, reference bodies having markers are associated with the first and second bones to allow the position and orientation of the bones to be determined in the three dimensional coordinate system. The placement of a ligament graft is determined functionally and anatomically based upon the locations data, medical image data, and ultrasound data.

BRIEF DESCRIPTION OF THE DRAWINGS

The present invention is described below in relation to FIG. 1, which shows a ligament reconstruction system according to the invention.

DETAILED DESCRIPTION OF THE PREFERRED EMBODIMENT

Figure 1:
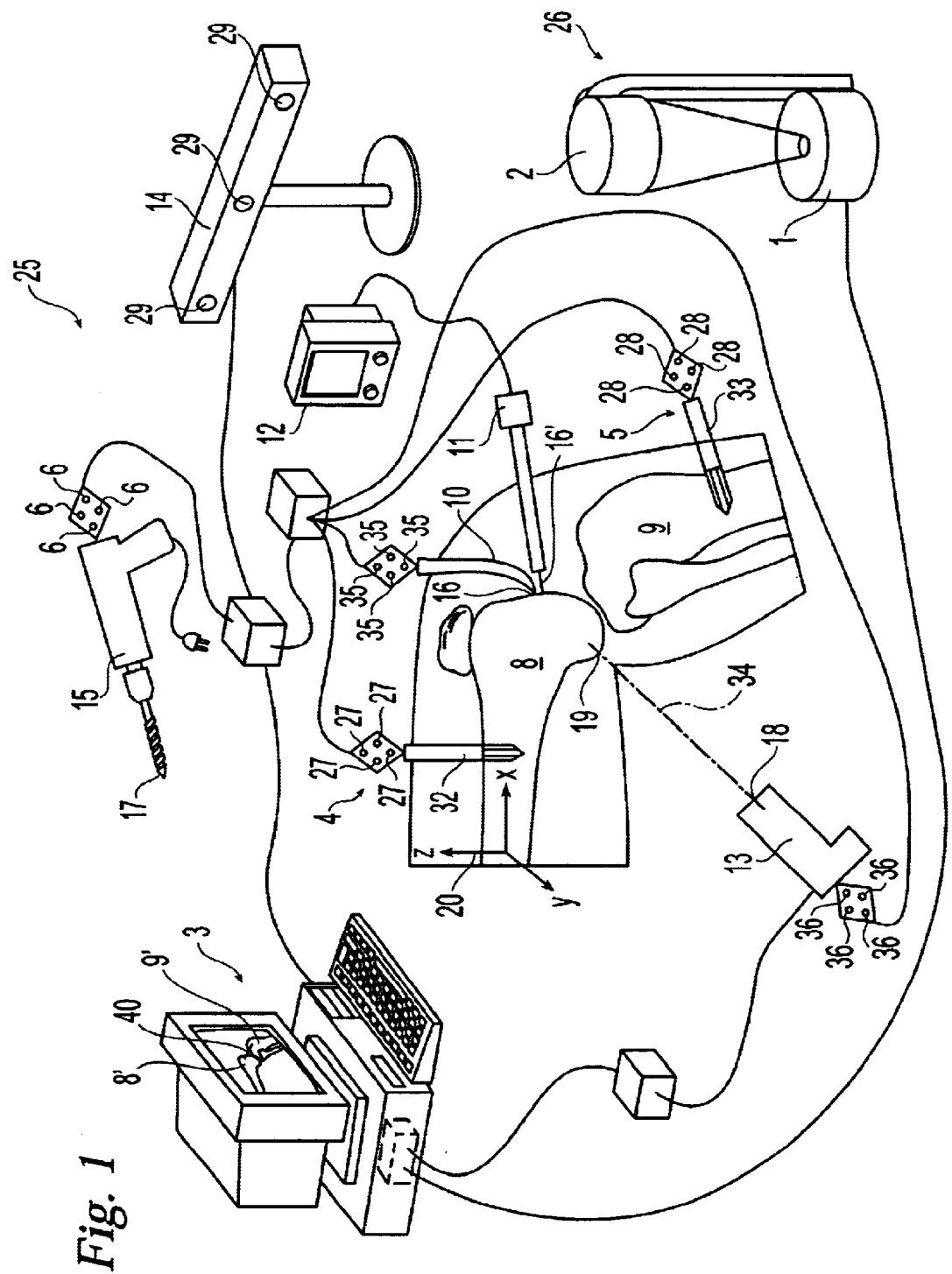

Referring to FIG. 1, a ligament reconstruction system 25 is configured for performing ligament reconstruction or other restorative procedure involving a joint, such as a knee, of an individual. System 25 preferably includes a positioning measuring device 14, which is configured to determine the position and orientation of an object in a three dimensional coordinate system 20, which preferably includes at least a first and second bone of an individual. The first and second bones are preferably the individual's femur 8 and tibia 9.

Determining the position and orientation of an object is referred to herein as "tracking" the object. Tracking an object preferably involves determining the position of at least two and preferably three or more markers associated with the object. The markers preferably have a known spatial relationship relative to the object to be tracked. Based on the known spatial relationship, the position and orientation of the object can be determined based upon the positions of the associated markers. Device 14 is in communication with computer 3 to allow the position and orientation of a tracked object to be thereby displayed.

In a preferred embodiment, the markers are configured to emit energy and position measuring device 14 is configured with at least three energy detection elements 29 to detect energy emitted by the markers. For example, energy emitting markers can include light sources, such as light emitting diodes, which emit in the visible or infrared, acoustic transmitters, or conductive coils suitable for establishing a detectable magnetic field. The energy detection elements can include, for example, light detectors 29, such as photodiodes or charge coupled devices. A suitable position measurement device is the OPTOTRAK 3020 available from Northern Digital, Canada. The OPTOTRAK device tracks the position of infrared light emitting diodes, which are positioned in a known spatial relationship to objects to be tracked. It should be understood, however, that tracking can be accomplished where the markers are configured to detect energy and the position measuring device is configured to emit energy to be detected by the markers.

A drilling device 15 having at least three markers 6 is an example of an object trackable by position measuring device 14. The drilling device has a drill tip 17 having a known spatial relationship relative to markers 6. Position measuring device 14 determines the position and orientation of markers 6 in the three dimensional coordinate system. Based upon the known spatial relationship between drill tip 17 and markers 6, the position of drill tip 17 is determined.

Computer 3 is preferably configured to allow at least one of medical image data and ultrasound data, which are described below, to be used in planning the position and orientation (path) of a hole to be drilled in a bone. The path of a hole being bored by the drill can be monitored and displayed by the computer. Thus, the actual path can be compared to the previously planned drill path to allow the practitioner to minimize deviations between the actual procedure and the preoperative plan. In one embodiment the drill is guided to allow the computer to control the drilling path.

Ligament reconstruction system 25 also includes a plurality of reference bodies 4, 5, for determining the position and orientation of an individual's bone in the three dimensional coordinate system. The reference bodies 4, 5 are preferably rigid and include respective markers 27, 28, which are preferably configured to emit energy. Each reference body 4, 5 preferably includes a respective attachment element, such as pins or screws 32, 33, with which the reference bodies can be releasably attached to a bone. For example, reference body 4 is shown as being attached to femur 8. The position and orientation of femur 8 can be determined based upon the position and orientation of markers 27 attached thereto.

System 25 also includes a pointer 10 and endoscope 11, which cooperate to allow a practitioner to digitize landmarks of the femur 8 and tibia 9. Digitizing a landmark comprises determining the position of the landmark in the three dimensional coordinate system, as discussed below. Pointer 10 includes markers 35, which allow the position and orientation of the pointer to be determined in the three dimensional coordinate system. The pointer preferably includes a pointer tip 16 having a known spatial relationship to the markers 35.

Based upon the known spatial relationship, the position of the pointer tip 16 can be determined from the position and orientation of the markers 35.

To digitize a landmark, such as a point associated with an individual's bone, pointer tip 16 is positioned to have a known spatial relationship to the landmark to be digitized. Preferably, pointer tip 16 is positioned to touch the landmark. A display 12 of endoscope 11 allows the practitioner to visualize the pointer tip 16 and the landmark. Display 12 can be integrated with a display of computer 3. The position in the three dimensional coordinate system of the landmark to be digitized is determined from the position of pointer tip 16, which is determined as described above. In a preferred embodiment, the pointer and endoscope are integrated. The integrated pointer-endoscope includes an endoscopic palpation hook 16'.

Certain landmarks, such as the posterior femoral and tibial condyles, are difficult to obtain by direct digitization with the pointer 10. For this reason, the device according to the invention preferably includes an A-mode ultrasound device 13 equipped with markers 36. Ultrasound device 13, which is in communication with computer 3, determines the distance between an ultrasound device head 18 and an intersection point 19 of an ultrasound beam 34 with the surface of a bone. Because the position and orientation of ultrasound device head 18 is determined by position measuring device 14, the orientation of beam ultrasound beam 34 can also be determined. The orientation of ultrasound beam 34 and the distance of ultrasound device head 18 from intersection point 19 are used to determine the position of intersection point 19 within the three-dimensional coordinate system 20 by means of a coordinate transformation performed via the computer 3.

Intraoperatively measured landmarks on the surface of a patient's bone are used to establish a mathematical relationship between the intraoperative position of the bone and an image of the bone as represented by the medical image data. Such a transformation of coordinates on the medical image may be computed into coordinates within the on-site three dimensional coordinate system 20 therewith allowing functional and anatomical considerations of the graft placement.

System 25 includes a medical imaging device 26 for obtaining medical image data. Medical imaging device 26 preferably includes an X-ray source 1 and an X-ray receiver 52 suitable for acquiring medical image data in the form of X-rays of a patient's anatomy. Alternatively, the medical image data can comprise images obtained using with other imaging technologies such as magnetic resonance. In any case, the medical image data can be obtained pre-operatively and/or intra-operatively. Preoperative medical image data will typically be available in either numerical or analog formats. Where the medical image data are available in numerical format, such as in digitized format, the medical image data can be transferred directly to a computer 3. Where the medical image data are available in an analog format, such as a radiographic image, the image can be scanned, digitized and transferred to computer 3.

To obtain intra-operative medical image data, medical imaging device 26 preferably includes a fluoroscope. Intra-operative medical image data are preferably obtained of standard orientations, such as, for example, anterior-posterior and medial-lateral orientations. The medical image data preferably include an image of a sizing element, such as a ruler having radio-opaque markings. Images of the radio-opaque markings appear in the medical image data. Computer 3 is configured to determine the magnification of the medical image data, such as an image of a knee, based upon the images of the radio-opaque markings.

Computer 3 may be used to display an image 8' of the femur and an image 9' of the tibia. When ligament attachment points are identified, the computer can display a preferably three dimensional representation of the connection 40 between ligament attachment points previously determined using the pointer or ultrasound device. The medical image data are preferably prepared as X-rays templates. Desired ligament placement with respect to anatomical landmarks, e.g. the medial and lateral condyles or the trochlea, can be planned directly on the medical image displayed via computer 3 through manipulations of the templates.

While the above invention has been described with reference to certain preferred embodiments, it should be kept in mind that the scope of the present invention is not limited to these. Thus, one skilled in the art may find variations of these preferred embodiments which, nevertheless, fall within the spirit of the present invention, whose scope is defined by the claims set forth below.

What is claimed is:

1. A method for obtaining data indicative of a location for ligament graft placement, comprising;
   providing medical image data representative of at least a first bone and a second different bone;
   irradiating the first bone with ultrasound emitted by an ultrasound emitter;
   receiving at least some of the emitted ultrasound;
   detecting energy emitted by a first set of energy emitters to determine a position of the ultrasound emitter;
   determining, based on the received ultrasound and the position of the ultrasound emitter, first position data indicative of an intraoperative position of at least one point of a first set of points associated with a surface of the first bone, the first set of points comprising at least one member;
   determining a mathematical relationship between the medical image data and the first position data;
   tracking the intraoperative position of the at least one point of the first set of points by detecting energy emitted from a second set of energy emitters:
   determining second position data indicative of an intraoperative position of at least one point of a second set of points associated with a surface of the second bone, the second set of points comprising at least one member;
   determining a mathematical relationship between the medical image data and the second position data;
   tracking the intraoperative position of the at least one point of the second set of points by detecting energy emitted from a third set of energy emitters;
   determining the data indicative of the location for ligament graft placement on the basis of the medical image data and the first and second sets of position data; and
   displaying a representation of a connection between at least one of the points of the first set of points and at least one of the points of the second set of points.

2. The method of claim 1, wherein the first set of points comprises at least one of a posterior femoral condyle and a tibial condyle.

3. The method of claim 1, wherein the medical image data comprises a preoperative X-ray.

4. The method of claim 1, wherein the medical image data comprises an intraoperative X-ray.

5. The method of claim 1, wherein the first bone is a tibia.

6. The method of claim 1, wherein the first bone is a femur.

7. The method of claim 1, wherein the method comprises:
   contacting at least one point associated with the surface of the first bone with a pointer;
   detecting energy emitted by a third set of energy emitters to thereby determine an intraoperative position of the pointer; and
   determining the intraoperative position of the at least one point based upon the intraoperative position of the pointer.

8. The method of claim 7, wherein the pointer is integral with an endoscope.

9. The method of claim 1, further comprising:
   detecting energy emitted by a third set of energy emitters to thereby determine an intraoperative position of a drill; and
   drilling a hole in the first bone, the hole being drilled along a drill path determined using the data indicative of a location for ligament graft placement.

10. The method of claim 1, wherein the first and second sets of energy emitters comprise different energy emitters.

11. The method of claim 1, wherein the connection is a representation of a ligament.

12. The method of claim 1, wherein detecting energy emitted by the first and second sets of energy emitters comprises detecting light.

13. A system for obtaining data indicative of a location for ligament graft placement with respect to at least a first bone, the system comprising:
   a position determining device comprising first, second, and third sets of energy emitters and a plurality of energy receivers configured to receive energy emitted by the first and second sets of energy emitters;
   at least a first reference body, the first set of energy emitters operably associated with the first reference body;
   a second reference body, the third set of energy emitters operably associated with the second reference body;
   an ultrasound emitter configured to irradiate the first bone with ultrasound and to receive a portion of the ultrasound;
   a computer configured to:
      receive medical image data of first and second different bones;
      determine an intraoperative position of the ultrasound emitter based upon energy received from the second set of the energy emitters;
      determine, based upon the received ultrasound and the intraoperative position of the ultrasound emitter, first position data indicative of an intraoperative position of at least one point of a first set of points associated with a surface of the first bone, the first set of points having at least one member;
      determine a mathematical relationship between the medical image data of the first bone and the first position data;
      track the intraoperative positions of the at least one point of the first set of points based upon energy received from the first set of energy emitters;
      determine second position data indicative of an inoperative position of at least least one point of a second set of points associated with a surface of the second bone, the second set of points having at least one member;

determine a mathematical relationship between the medical image data of the second bone and the second position data;

track the intraoperative positions of the at least one point of the second sets of points based upon energy received from the third set of energy emitters;

display a three-dimensional representation of a connection between at least one point of the first set of points and at least one point of the second set of points; and wherein the computer is further configured to obtain the data indicative of the location for ligament graft placement based on the intraoperative positions of the first and second position data and the medical image data.

14. The system of claim 13, wherein the medical image data comprise an X-ray.

15. The system of claim 14, further comprising an X-ray source and an X-ray receiver configured to obtain the X-ray.

16. The system of claim 13, wherein the first and second sets of energy emitters comprise light emitting diodes.

17. The system of claim 13, wherein the connection is a representation of a ligament.

18. A system for obtaining data indicative of a location for ligament graft placement with respect to at least a first bone and a second bone, the system comprising:

a position determining device comprising first and second sets of energy emitters and a plurality of energy receivers configured to receive energy emitted by the first and second sets of energy emitters;

at least a first reference body, the first set of energy emitters operably associated with the first reference body;

a pointer comprising a pointer portion configured to contact a surface of at least one of the first and second bones, wherein the second set of energy emitters and the pointer portion have a known spatial relationship;

a computer configured to:
  determine an intraoperative position of the pointer based upon energy received from the second set of energy emitters;
  determine, based upon the intraoperative position of the pointer and the known spatial relationship, first position data indicative of an intraoperative position of at least one point of a first set of points contacted by the pointer portion, the first set of points having at least one member and being associated with the surface of the first bone;
  determine, based upon the intraoperative position of the pointer and the known spatial relationship, second position data indicative of an intraoperative position of at least one point of a second set of points contacted by the pointer portion, the second set of points having at least one member and being associated with the surface of the second bones
  determine a mathematical relationship between the medical image data of the first bone and the first position data;
  determine a mathematical relationship between the medical image data of the second bone and the second position data;
  track the intraoperative positions of the at least one point of the first set of points based upon energy received from the first set of energy emitters;
  display a representation of a connection between at least one of the points of the first set of points and at least one of the points of the second set of points; and wherein the computer is further configured to obtain the data indicative of the location for ligament graft placement based on the first position data and the medical image data.

19. The system of claim 18, wherein the pointer is integral with an endoscope.

20. The system of claim 18, wherein the first and second sets of energy emitters comprise light emitting diodes.

21. The system of claim 4, wherein the connection is a three dimensional representation of a connection between at least one of the points of the first set of points and at least one of the points of the second set of points.

22. A method for obtaining data indicative of a location for ligament graft placement, comprising:

providing medical image data representative of a first bone;

providing medical image data representative of a second, different bone;

contacting the first bone with a pointer;

detecting energy emitted by a first set of energy emitters to determine a position of the pointer;

determining, based on the position of the pointer, first position data indicative of an intraoperative position of at least one point of a first set of points associated with a surface of the first bone, the first set of points having at least one member;

determining a mathematical relationship between the medical image data and the first position data;

tracking the intraoperative positions of the at least one point of the first set of points by detecting energy emitted from a second set of energy emitters;

determining second position data indicative of an intraoperative position of at least one point of a second set of points associated with a surface of the second bone, the second set of points comprising at least one member;

determining a mathematical relationship between the medical image data and the second position data;

tracking the intraoperative position of the at least one point of the second set of points by detecting energy emitted from a third set of energy emitters;

determining the data indicative of the location for ligament graft placement on the basis of the medical image data and the first and second position data; and displaying a representation of a connection between at least one of the first set of points and at least one of the second set of points.

23. The method of claim 22, wherein the connection is a representation of a ligament.

24. The method of claim 22, wherein the pointer is integral with an endoscope.

25. The method of claim 22, further comprising:

detecting energy emitted by a fourth set of energy emitters to thereby determine an intraoperative position of a drill; and drilling a hole in the bone, the hole being drilled along a drill path determined using the data indicative of a location for ligament graft placement.

26. The method of claim 22, wherein detecting energy emitted by the first and second sets of energy emitters comprises detecting light.

27. A system for obtaining data indicative of a location for ligament graft placement with respect to at least first and second bones, the system comprising:

a position determining device comprising first, second, and third sets of energy emitters and a plurality of energy receivers configured to receive energy emitted by the first, second, and third sets of energy emitters;

at least first and second reference bodies, the first and second sets of energy emitters operably associated with the first and second reference bodies, respectively;

an ultrasound emitter configured to irradiate the first bone with ultrasound and to receive a portion of the ultrasound;

a computer configured to:
receive medical image data of the first and second bones;

determine an intraoperative position of the ultrasound emitter based upon energy received from the third set of the energy emitters;

determine, based upon the received ultrasound and the intraoperative position of the ultrasound emitter, first position data indicative of an intraoperative position of at least one point of a first set of points associated with a surface of the first bone, the first set of points having at least one member;

determine second position data indicative of an intraoperative position of at least one point of a second set of points associated with a surface of a second bone, the second set of points having at least one member;

determine a mathematical relationship between the medical image data of the first and second bones and the first and second position data;

track the intraoperative positions of the at least one point of the first set of points based upon energy received from the first set of energy emitters;

track the intraoperative positions of the at least one point of the second set of points based upon energy received from the second set of energy emitters; and wherein the computer is further configured to (a) provide the data indicative of the location for ligament graft placement based on the intraoperative positions of the first and second position data and the medical image data and (b) display a representation of a connection between at least one of the first set of points and at least one of the second set of points.

* * * * *